United States Patent

Strassburg et al.

[11] Patent Number: 5,399,155
[45] Date of Patent: Mar. 21, 1995

[54] STATIC ANKLE PLANTAR-FLEXION PREVENTION DEVICE

[76] Inventors: Terry A. Strassburg, 1153 Oliver St., North Tonawanda, N.Y. 14120-2639; John J. Stachura, 4565 Bailey Ave., Buffalo, N.Y. 14226

[21] Appl. No.: 83,890
[22] Filed: Jun. 28, 1993
[51] Int. Cl.6 .............................................. A41F 5/00
[52] U.S. Cl. .............................................. 602/28; 2/239
[58] Field of Search ..................... 2/239; 602/4, 5, 23, 602/24, 27, 32, 28; 482/907

[56] References Cited

U.S. PATENT DOCUMENTS 4,559,934 12/1985 Philipp ................................. 602/27

*Primary Examiner*—Clifford D. Crowder
*Assistant Examiner*—Gloria Hale

[57] ABSTRACT

This invention relates to a device for the maintaining of the Plantar Fascia (aproneurosis) in a neutral to slight dorsiflexion by means of passive static tension, thus not allowing it to contract. This device consists of a (1) over the calf sock, (2) a reinforced adjustable support strap attached around the upper portion of the sock with a "D" ring attached to the front (shin) side, (3) a reinforced inelastic adjustable strap attached to the toe of the sock, with a hook and loop assembly attached for closure. When this strap is passed thru the "D" ring and secured by means of the hook and loop assembly, the Plantar Fascia can be maintained in the desired position.

This device is of simple construction and uses only minimal adjustments to achieve and maintain the plantar aproneurosis in a neutral to slight dorsiflexion. Further it does not lock the ankle joint, thus allowing some medial or lateral movement of the subtalar joints. Also no attempt is made to prevent promation of the forefoot.

The device is designed to be a supplemental form of treatment that, when worn at night or during extended periods of inactivity can, in conjunction with traditional treatment, significantly reduces the recovery time in the treatment of plantar fasciitis.

7 Claims, 4 Drawing Sheets

STATIC ANKLE PLANTAR-FLEXION PREVENTION DEVICE

BACKGROUND

1. Field of Invention

This invention relates to calcanial spur's more commonly referred to as heel spur's and a device that when worn, promotes and speeds the healing when used along with the more traditional treatments.

2. Discription of Established Treatments

On the sole of one's foot is a thick fibrous material called the "plantar aponeurosis or fascia". It originates at the medial tuberosity of the calcaneus (heel bone) and spreads out over the sole of the foot and terminates in the ligamentous structures near the metartarsal heads in the forefoot. The plantar aponeurosis, by its design, covers all of the soft tissue structures on the sole of the foot. It provides static support and acts like a bowstring in support of the medial longitudinal arch of the foot. Movements within the ankle and foot are very complex and require various amounts of freedom of movement. The plantar aponeurosis helps check motion within the joints of the ankle and forefoot. When these joints are stressed, the plantar aponeurosis may become inflamed and painful and facciitis may result.

Plantar Fasciitis (heel spur syndrome) is a common problem among people whose occupation entail a great deal of walking or standing or who are active in sports. A calcanial spur is described as a bony growth on the lower surface of the heel bone (calcaneus). Some contributing factors to this condition are: flat feet, high arches, ridgid feet, poor shoe support, increased age, sudden weight increase, sudden increase in activity or after return from a period of inactivity and even family history. The problem may begin as a dull intermittent pain in the heel and progress to a sharp persistant pain. It is most often worse at the beginning of a sporting activity and with the first few steps after sitting or standing. It is most noticeably worse in the morning when first getting out of bed and it is mainly, but not exclusively, to this aspect that this invention is directed.

In seeking relief from the pain of heel spurs the traditional treatment varies from rest to medication (including steroids) to physical therapy to orthosis or even surgical removal of the heel spur. While this device does not make the claim to be an exclusive remedy, it can be used in conjunction with the traditional treatments to enhance their effectiveness and possibly speed the recovery process. The nightly use of this device will provide an involuntary positive assist to the daily voluntary treatments.

HOW THE INVENTION WORKS

This device, when worn as prescribed, places the plantar aproneurosis in a state of passive, static, tension. While this tension is not of sufficient force so as to create a lengthening effect on the aponeurosis, it is of sufficient force so as to prevent it from contracting. This is achieved by holding the ankle and forefoot joints in a position of slight dorsiflexion and preventing the ankle and forefoot joints from adopting a position of plantarflexion. In this way, the plantar aponeurosis is not allowed to contract during the period that the device is being worn. The result is that after removal of the device by the wearer, and upon bearing weight on the effected foot, the plantar aponeurosis will not be placed in pathologic tension thus reducing and/or eliminating pain.

OBJECTIVES

The primary objective of this device is to maintain the plantar aponeurosis in a neutral to slightly stretched position on an involuntary basis while sleeping or resting. The most noticeable residual effect of the device is the reduction or elimination of those first painful steps as one gets out of bed in the morning. In addition the involuntary stretching of the plantar aponeurosis over a longer period of time helps to strengthen the arch of the foot.

DESCRIPTION OF THE DEVICE

The device consists of an over the calf tube sock (A) attached to the top of which is an inelastic reinforcing strap (E). This inelastic reinforcing strap (E) measures twelve (12) inches by two (2) inches and is attached to the sock (A) by means of reinforced stitching. A "D" ring (C) is looped through the inelastic reinforcing strap (G) and attached at a lower end of the inelastic reinforcing strap (E). This places the "D" ring (C) at approximately the midline of the shin. A hook and loop assembly (F) is attached to the inelastic reinforcing strap (E) by means of reinforced stitching and aligned so closure takes place along the posterior of the sock (A). An inelastic strap (B) is attached to the "toe" end of the sock (A) by means of reinforced stitching. This inelastic strap (B) is ten (10) inches long and tapers from a width of $3\frac{1}{2}$ inches at the toe to $1\frac{1}{2}$ inches at the top. A hook and loop assembly (D) is attached to the inelastic strap (B) at the upper end by means of standard stitching.

Figure 1:
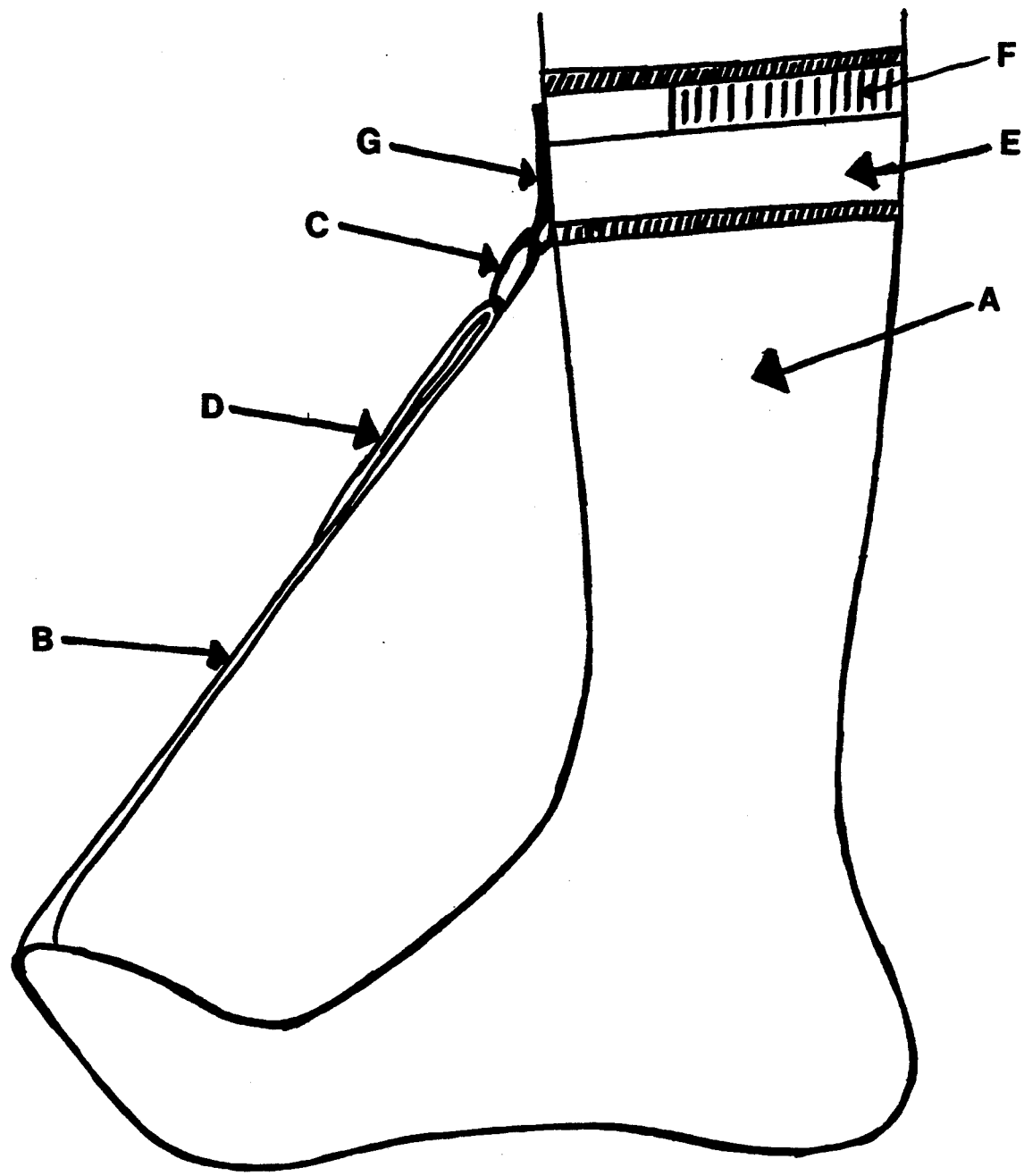
FIG. 1—Shows a lateral view of the sock.
Figure 2:
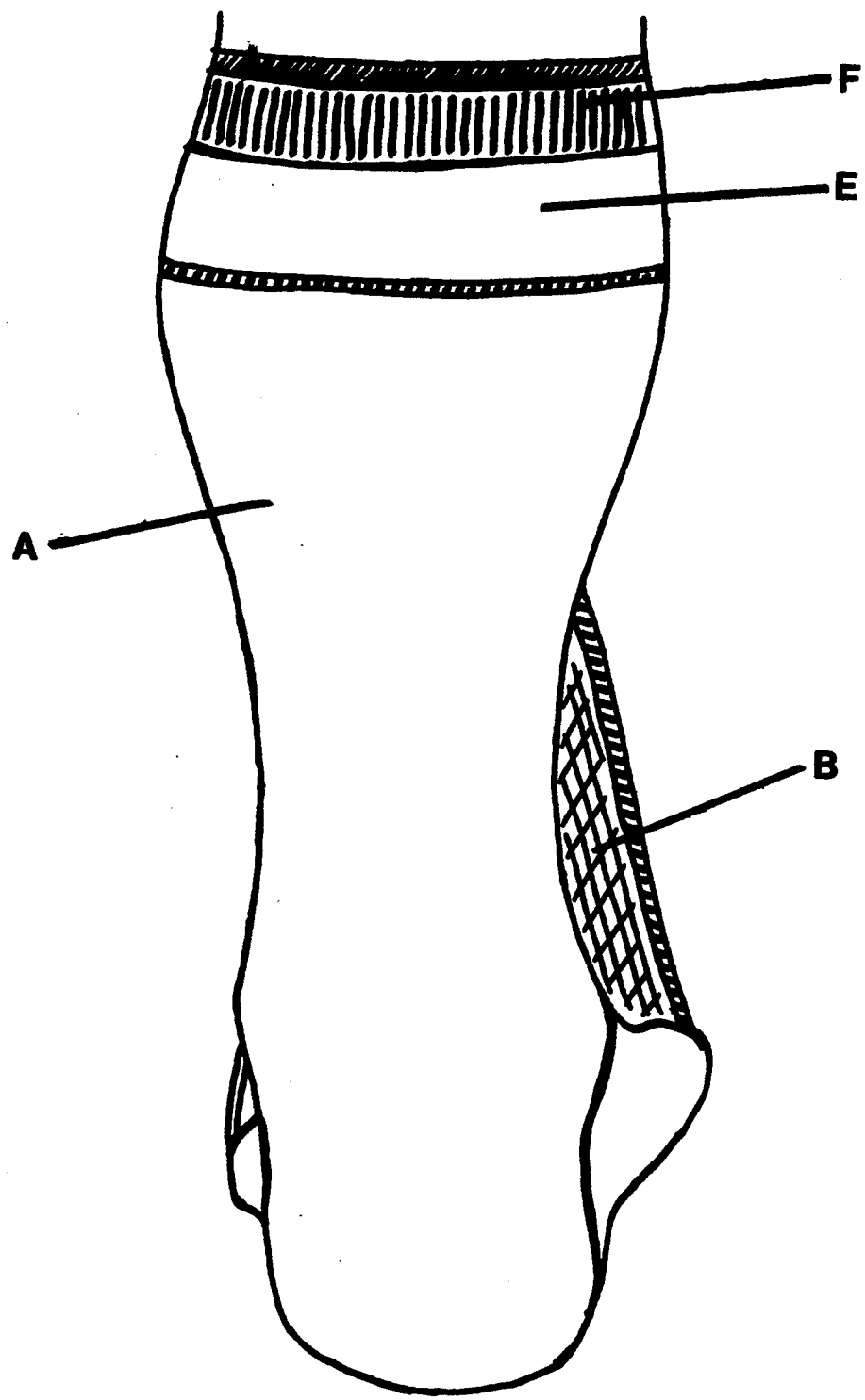
FIG. 2—Shows a posterior view of the sock.
Figure 3:
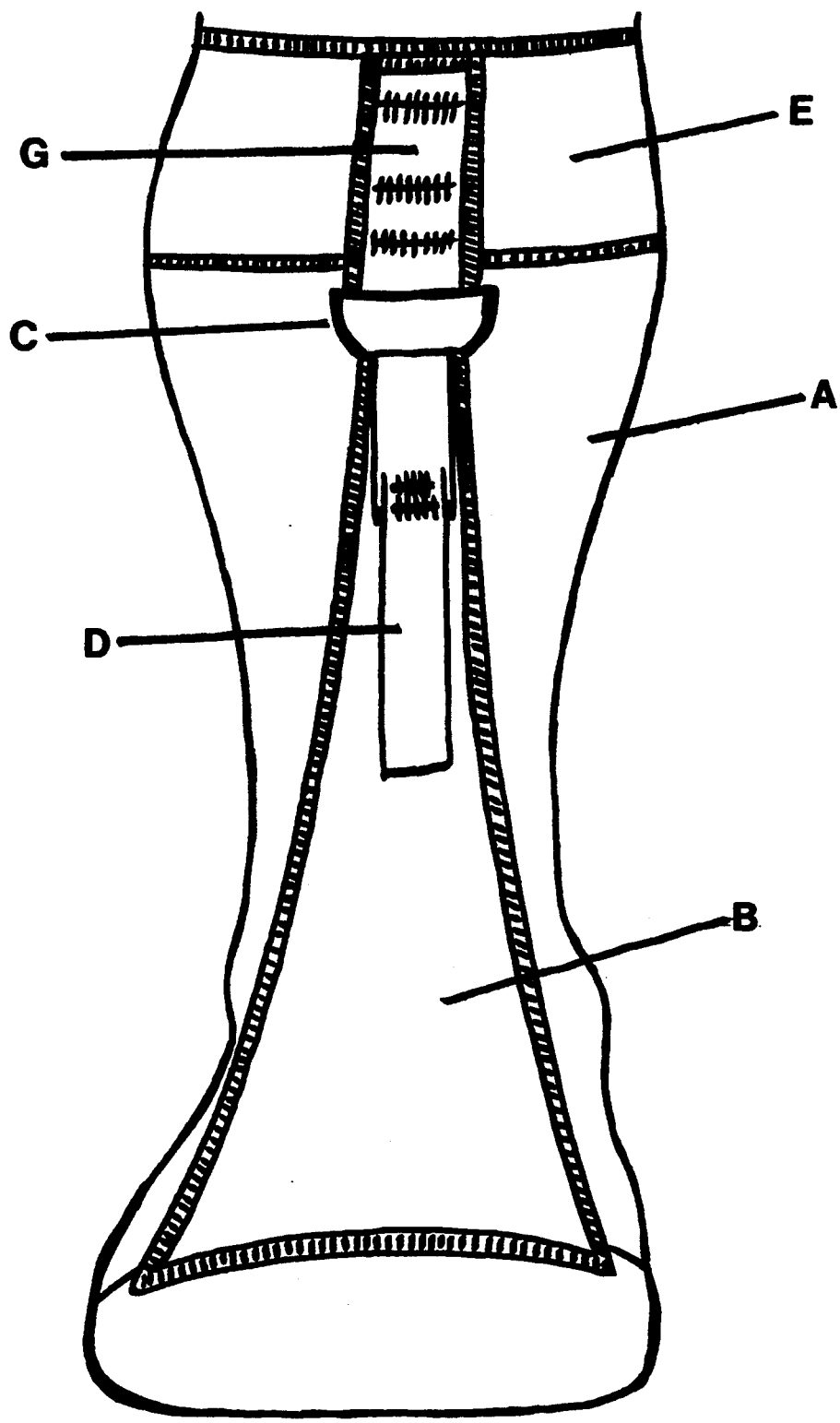
FIG. 3—Shows a front view of the sock.
Figure 4:
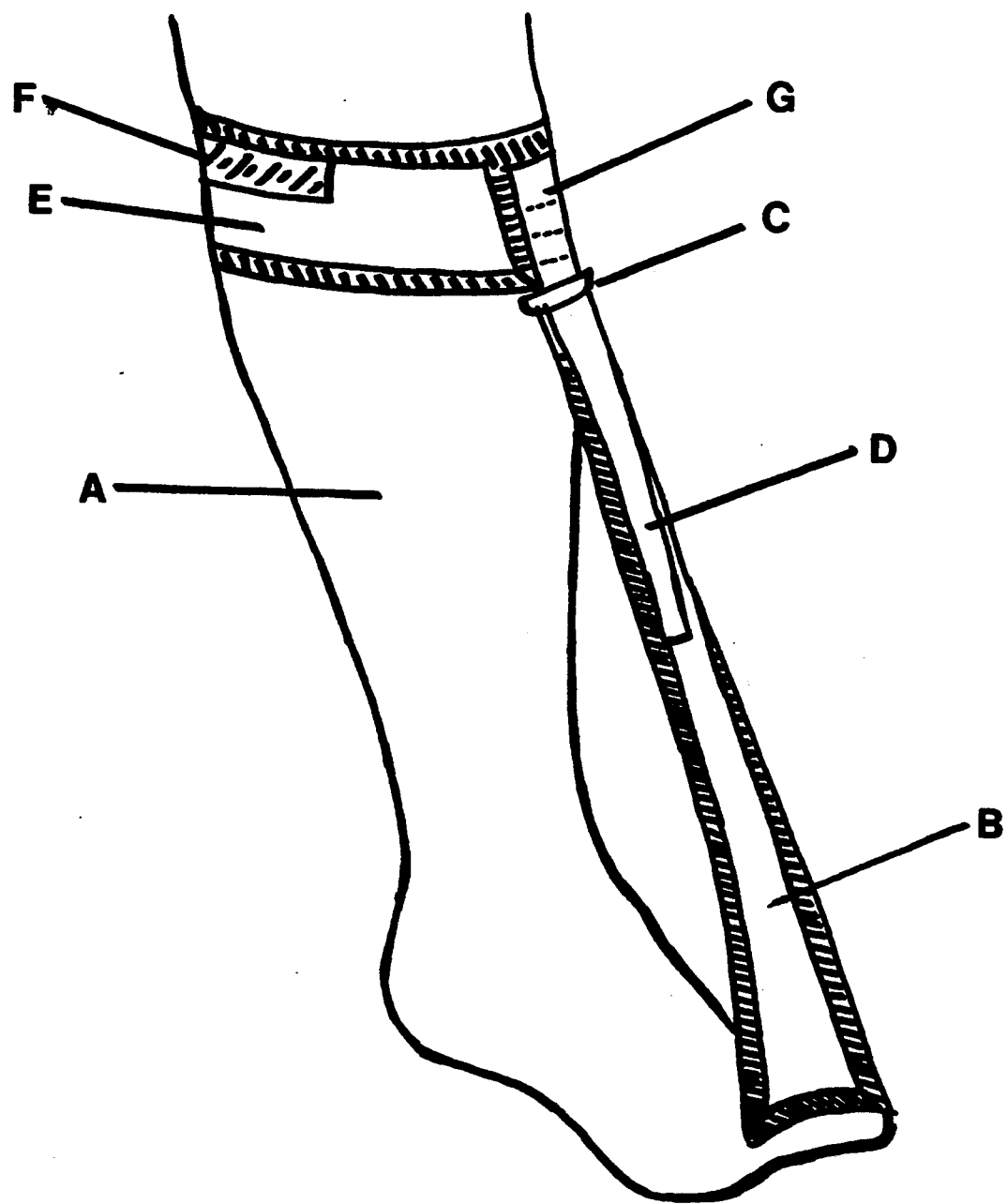
FIG. 4—Shows an oblique view of the sock.

The sock is put on in the normal way being sure to stretch it as high over the calf as possible with the "D" ring facing forward just below the knee (FIG. 3). Then the upper strap is secured around the leg (FIG. 3). The purpose of this strap is to help hold the "D" ring close to the leg and hold the sock in position. Then with the foot flat on the floor take the strap attached to the toe of the sock and pass it through the "D" ring from the bottom to the top (FIG. 4). Now pull up on the strap to lift the toes off of the floor and secure the hook and loop straps together in position (FIG. 5). The toes should be stretched upward but not so as to cause discomfort.

ADVANTAGES OF THIS DEVICE

1. It is very easy to use.
2. It has only minimum adjustments to be made for proper use.
3. It does not lock the ankle joint into any one position thus allowing some movement between the various joints preventing possible joint compression pain.
4. It can safely be worn for several hours without adverse effect when applied properly.
5. It can be worn to bed and provides no significant restrictions and will not interrupt normal sleep.
6. It is an effective device providing low cost relief of heel spur symptoms.

CONCLUSION

This device is designed so as to reduce and/or eliminate the pain associated with plantar fasciitis (heel spurs). This is achieved by the wearing of this device during a period of inactivity (such as at rest or sleep). Once the device is properly applied to the wearer, a static force is applied so as to prevent the plantar aponeurosis from contracting such as occured with ankle plantarflexion. The end result is the reduction and/or elimination of pain typically felt under the heel during weight bearing.

We claim:

1. A device for maintaining the Plantar Fascia and other structures on the Plantar surface of the foot in a neutral to slight dorsiflection thus limiting plantarflexion of the ankle wherein the device is comprised of:
   (a) an elastic sock adapted to fit tightly over the calf of the user with a hook or loop fastener component attached at the upper end of the sock;
   (b) an inelastic strap with one end connected to the toe of the sock and a hook and loop assembly at the other end for closure upon itself;
   (c) an inelastic strap reinforcing the top of the sock with a "D" ring connected thereon with a hook and loop assembly component for attaching the strap to the top of the sock and with a hook or loop fastener component at either end of the strap with the complementary fastener component at the other end of the strap for adjusting the tension of the strap to secure the "D" ring close to the leg of the wearer; and wherein when in use the strap connected to the toe of the sock is looped through the "D" ring at the top of the sock and closed upon itself.

2. A plantarflexion limiting device as in claim 1 wherein said sock is comprised of an elastic fabric that reaches above the calf of the wearer.

3. A plantarflexion limiting device as in claim 2 wherein said sock is comprised of an elastic fabric that is reinforced along a top edge with an inelastic strap measuring twelve inches by two inches that secures the sock to the leg above the calf.

4. A plantarflexion limiting device as in claim 3 wherein said inelastic strap reinforcing the top of said sock has a hook and loop assembly to secure the sock to the leg above the calf along its posterior margin.

5. A plantarflexion limiting device as in claim 1 wherein the inelastic strap connected to the toe of the sock is ten inches long and is secured to the toe end by stitching with the free end of the strap having a hook and loop assembly thereon.

6. A plantarflexion limiting device as in claim 1 wherein said "D" ring is attached at the upper forward shin surface of said sock at a bottom edge of the reinforcing inelastic strap.

7. A plantarflexion limiting device as in claim 6 wherein the inelastic strap connected to the toe of the sock is secured through the "D" ring by the hook and loop assembly six inches along its end.

* * * * *